(12) United States Patent
Margulis

(10) Patent No.: US 7,518,094 B2
(45) Date of Patent: Apr. 14, 2009

(54) COMPENSATION OF NONUNIFORMITY AMONG MULTIPLE SENSING DIODES IN A MULTIPLE SENSOR DEVICE

(75) Inventor: Pavel Margulis, Ashdod (IL)

(73) Assignee: Applied Materials, Israel, Ltd., Rehovot (IL)

( * ) Notice: Subject to any disclaimer, the term of this patent is extended or adjusted under 35 U.S.C. 154(b) by 24 days.

(21) Appl. No.: 11/446,647

(22) Filed: Jun. 5, 2006

(65) Prior Publication Data

US 2007/0278382 A1 Dec. 6, 2007

(51) Int. Cl.
*H03F 3/08* (2006.01)
(52) U.S. Cl. .................................. 250/214 A
(58) Field of Classification Search .............. 250/208.1, 250/208.2, 214 R, 214 A, 214 AG, 214 DC; 330/59, 69, 147, 199, 308; 327/514
See application file for complete search history.

(56) References Cited

U.S. PATENT DOCUMENTS

| | | | | |
|---|---|---|---|---|
| 4,144,036 A | * | 3/1979 | Cummings | 44/407 |
| 4,574,249 A | * | 3/1986 | Williams | 330/59 |
| 5,708,471 A | * | 1/1998 | Okumura | 348/301 |
| 6,242,732 B1 | * | 6/2001 | Rantakari | 250/214 A |
| 6,330,303 B1 | * | 12/2001 | Yamane et al. | 378/98.8 |
| 6,417,503 B1 | * | 7/2002 | Tsuruta | 250/214 A |
| 6,455,839 B1 | * | 9/2002 | O'Connor et al. | 250/221 |
| 6,707,023 B2 | * | 3/2004 | Fong et al. | 250/214 A |
| 6,851,849 B2 | * | 2/2005 | Kimura | 374/163 |
| 6,864,751 B1 | * | 3/2005 | Schmidt et al. | 330/311 |
| 7,173,230 B2 | * | 2/2007 | Charbon | 250/214 A |
| 2005/0052231 A1 | * | 3/2005 | Schmidt et al. | 330/98 |

FOREIGN PATENT DOCUMENTS

JP 10335948 A * 12/1998

* cited by examiner

*Primary Examiner*—Thanh X Luu
(74) *Attorney, Agent, or Firm*—Tarek N. Fahmi

(57) ABSTRACT

A method and system for the compensation of nonuniformity among a plurality of light sensing diodes adapted to convert light to a current output. A system embodiment includes a plurality of trans-impedance amplifier circuits, each trans-impedance amplifier circuit having an op-amp, and an impedance connecting an output of the op-amp to a first input of the op-amp, and a plurality of variable voltage source. The current output of each sensing diode is coupled to a corresponding trans-impedance amplifier circuit by an electrical connection to the first input of corresponding op-amp. A second input of the corresponding op-amp is coupled to a corresponding adjustable voltage source. The output of the corresponding op-amp is a signal responsive to a sensing voltage, and to a voltage signal provided by the corresponding adjustable voltage source, the sensing voltage being responsive to the current output of a corresponding sensing diode. Changes in a voltage signal provided by the corresponding adjustable voltage source affect a characteristic of the corresponding sensing diode.

6 Claims, 5 Drawing Sheets providing multiple sensing diodes adapted to convert light to current. Each sensing diode is coupled to an output circuit that includes a trans-impedance amplifier connected to an adjustable voltage source.
210 determining a voltage signal provided by each of the adjustable voltages sources such as to affect a sensing diode characteristic.
220.

adjusting the adjustable voltage sources according to the determination.
230 illuminating a wafer or a reticle and providing multiple output signals, whereas each output signal is responsive to a current that flows through a sensing diode and to a voltage signal provided by an adjustable voltage source coupled to that sensing diode.
240 includes illuminating a wafer or a reticle and providing multiple output signals, wherein each output signal is responsive to a current that flows through a sensing diode.
250

COMPENSATION OF NONUNIFORMITY AMONG MULTIPLE SENSING DIODES IN A MULTIPLE SENSOR DEVICE

FIELD OF THE INVENTION

This invention relates to systems and methods for controlling the characteristics of multiple sensors.

BACKGROUND OF THE INVENTION

Integrated circuits are very complex devices that include multiple layers. Each layer may include conductive material, isolating material while other layers may include semi-conductive materials. These various materials are arranged in patterns, usually in accordance with the expected functionality of the integrated circuit. The patterns also reflect the manufacturing process of the integrated circuits.

Integrated circuits are manufactured by complex multi-staged manufacturing processes. During this multi-staged process resistive material is (i) deposited on a substrate/layer, (ii) exposed by a photolithographic process, and (iii) developed to produce a pattern that defines some areas to be later etched.

Various metrology, inspection and failure analysis techniques evolved for inspecting integrated circuits both during the fabrication stages, between consecutive manufacturing stages, either in combination with the manufacturing process (also termed "in line" inspection techniques) or not (also termed "off line" inspection techniques). Various optical as well as charged particle beam inspection tools and review tools are known in the art, such as the Elite™, UVision™, Complus™ and SEMVision™ of Applied Materials Inc. of Santa Clara, Calif.

A typical inspection tool includes multiple sensor that convert received light to an electrical signal, such as to enable electrical components such as image processors to process the receives signals and to evaluate the stat of an inspected object.

Two commonly used sensors include the reverse biased solid state photo diode (PD) and the avalanche photo diode (APD). These diodes convert received light signals to current. Typically, these diodes are biased in a reverse voltage that can affect their characteristics.

The terminal capacitance of the biased solid state photo diodes is responsive to the reverse voltage while the gain of the avalanche photo diodes is responsive to the reverse voltage.

FIG. 1 illustrates a prior art multiple sensor unit 10. Multiple sensor unit 10 includes multiple (N) sensors. For convenience of explanation only it is assumed that N=9. The multiple sensor unit 10 can include biased solid state photo diodes or the avalanche photo diodes. For simplicity of explanation these diodes are referred to as sensing diodes.

Multiple sensor unit 10 includes multiple sensing diodes D1-DN 51-59. The anode of all these diodes is connected to the same electrode (at node A0 30).

The cathodes of diodes D1-DN 51-59 are connected (at output nodes A1-AN 41-49) to load resistors R1-RN 61-69. When light impinges on a certain sensing diode Dn then Dn outputs a current In that is translated to a voltage drop Voutn=In*Rn. This voltage is the output of the multiple sensor unit 10.

FIG. 2 illustrates another prior art multiple sensor unit 20. Multiple sensor unit 20 of FIG. 2 differs from the multiple sensor unit 10 of FIG. 1 by including a trans-impedance amplifier instead of a load resistor. This configuration is less noisy.

FIG. 2 illustrates two trans-impedance amplifiers, although each sensing diode is connected to its own trans-impedance amplifier. The first trans-impedance amplifier is connected to the cathode of D1 51 and includes an operational amplifier 71 that includes a positive input 171, a negative input 271 and an output 371. A resistor R1 81 is connected between the positive input 171 and the output 371. The negative input 271 is grounded so that the positive input 171 is virtually grounded. The current that flows through sensing diode D1 51 is converted to an output signal at 371.

The second illustrated trans-impedance amplifier is connected to the anode of DN 59 and includes an operational amplifier 79 that includes a positive input 179, a negative input 279 and an output 379. A resistor RN 89 is connected between the positive input 179 and the output 379. The negative input 279 is grounded so that the positive input 179 is virtually grounded. The current that flows through sensing diode DN 59 is converted to an output signal at 379.

The sensing diodes within a multiple sensor unit slightly differ from each other. The differences difference between the different sensing diodes is also known as sensing diode non-uniformity. This non-uniformity introduces errors in the detection and thus needs to be reduced. The prior art configurations of FIG. 1 and FIG. 2 are not adapted to compensate for these non-uniformities as all the sensing diodes are placed at the same reverse voltage.

There is a need to provide an efficient manner to control the characteristics of multiple sensors.

SUMMARY OF THE INVENTION

The invention provides a system that includes: multiple sensing diodes adapted to convert light to current; whereas each sensing diode is coupled to an output circuit that includes a trans-impedance amplifier coupled to an adjustable voltage source; wherein changes in a voltage signal provided by the adjustable voltage source affect a sensing diode characteristic.

Conveniently, the output signal outputs a signal that is responsive to a sensing voltage and to the voltage signal provided by the adjustable voltage source; wherein the sensing voltage is responsive to a current developed by the sensing diode.

Conveniently the system is a wafer inspection system or a reticle inspection system.

Conveniently the sensing diodes sense ultra-violet light.

Conveniently the output circuit further includes an operational amplifier stage, coupled to the trans-impedance amplifier and to the adjustable voltage source, adapted to output an output signal that is responsive to a sensing voltage that is responsive to a current developed by the sensing diode.

Conveniently the output circuit further includes an operational amplifier stage, coupled to the trans-impedance amplifier and to the adjustable voltage source, adapted to subtract the voltage signal provided by the adjustable voltage source from an internal voltage signal that is responsive to the voltage signal provided by the adjustable voltage source and to a sensing voltage that is responsive to a current developed by the sensing diode.

Conveniently the system includes a controller adapted to determine at least one diode characteristic and to adjust the adjustable voltage sources such as to compensate for sensing diodes non-uniformities.

The invention provides a method. The method includes: providing multiple sensing diodes adapted to convert light to current; whereas each sensing diode is coupled to an output circuit that comprises a trans-impedance amplifier coupled to an adjustable voltage source; determining a voltage signal provided by each of the adjustable voltages sources such as to affect a sensing diode characteristic.

Conveniently, the determining is followed by adjusting the adjustable voltage sources according to the determination.

Conveniently, the determining comprises determining the voltage signals provided by the adjustable voltages sources such as to compensate for non-uniformities between the sensing diodes.

Conveniently, the determining comprises measuring the sensing diodes non-uniformities.

Conveniently, the method further includes illuminating a wafer or a reticle and providing multiple output signals; wherein each output signal is responsive to a current that flows through a sensing diode and to a voltage signal provided by an adjustable voltage source coupled to that sensing diode.

Conveniently, the method further includes illuminating a wafer or a reticle and providing multiple output signals; wherein each output signal is responsive to a current that flows through a sensing diode.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 5 is a flow chart for a method according to an embodiment of the invention.

DETAILED DESCRIPTION OF THE DRAWINGS

Figure 1:
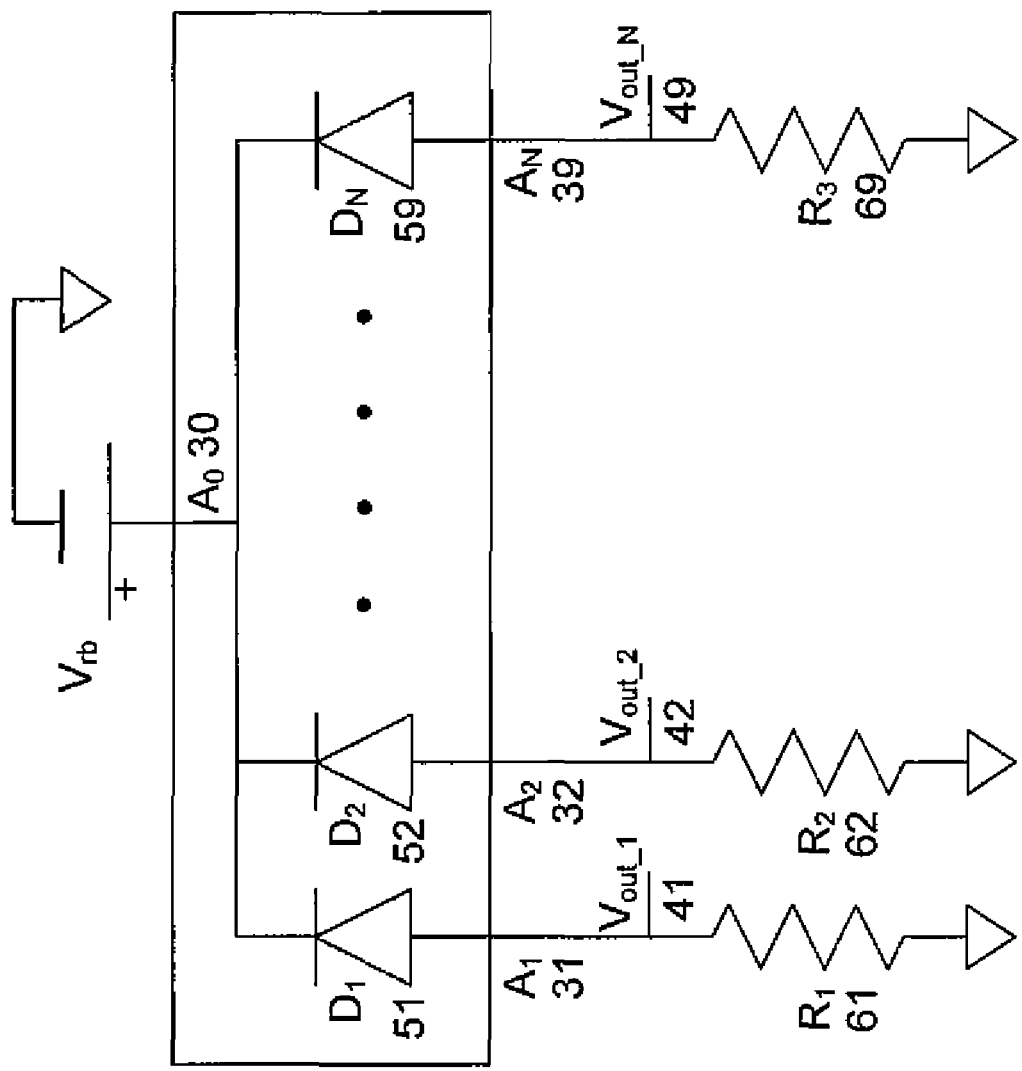
FIG. 1 illustrates a prior art multiple sensor unit.
Figure 2:
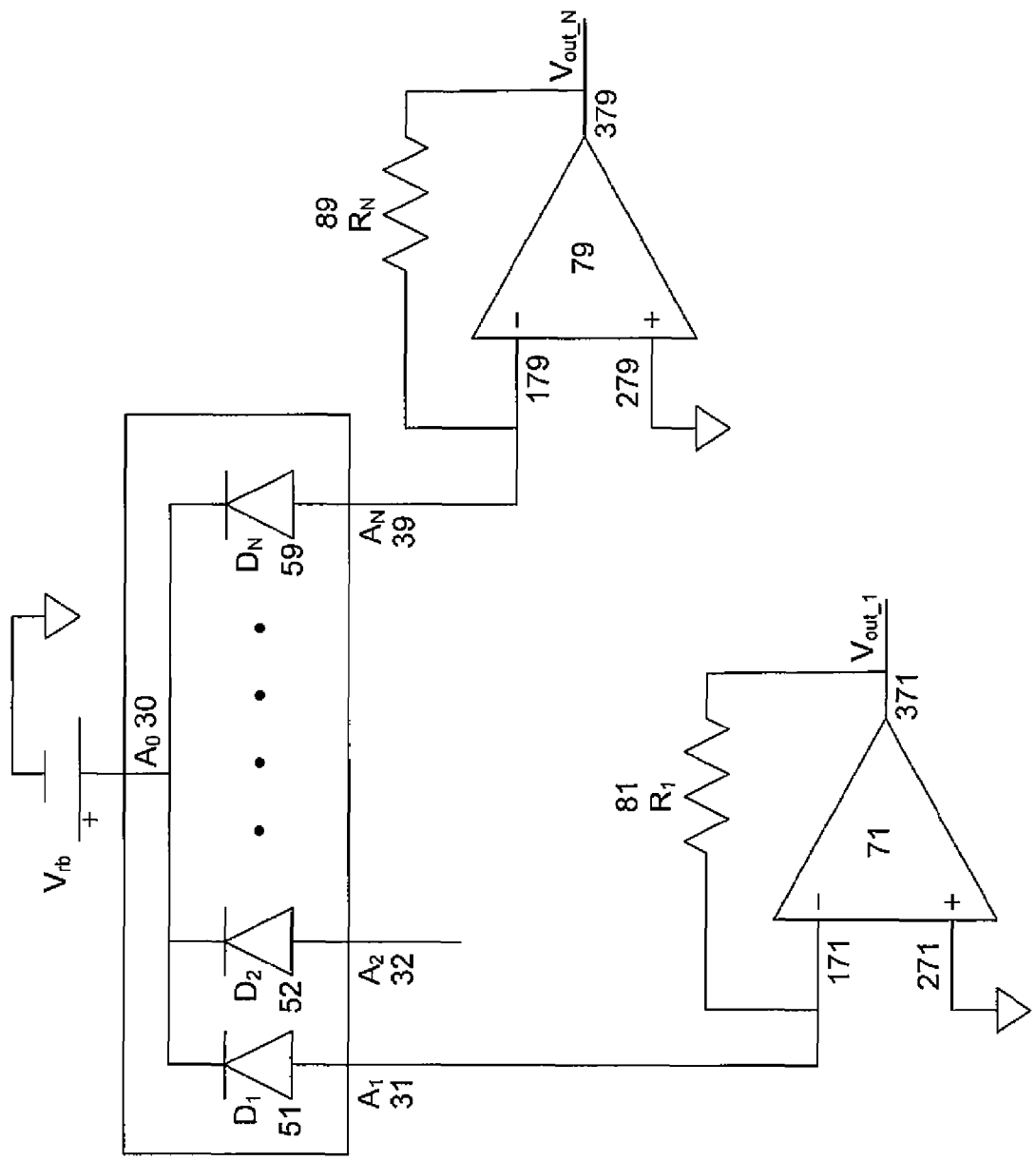
FIG. 2 illustrates another prior art multiple sensor unit.
Figure 3:
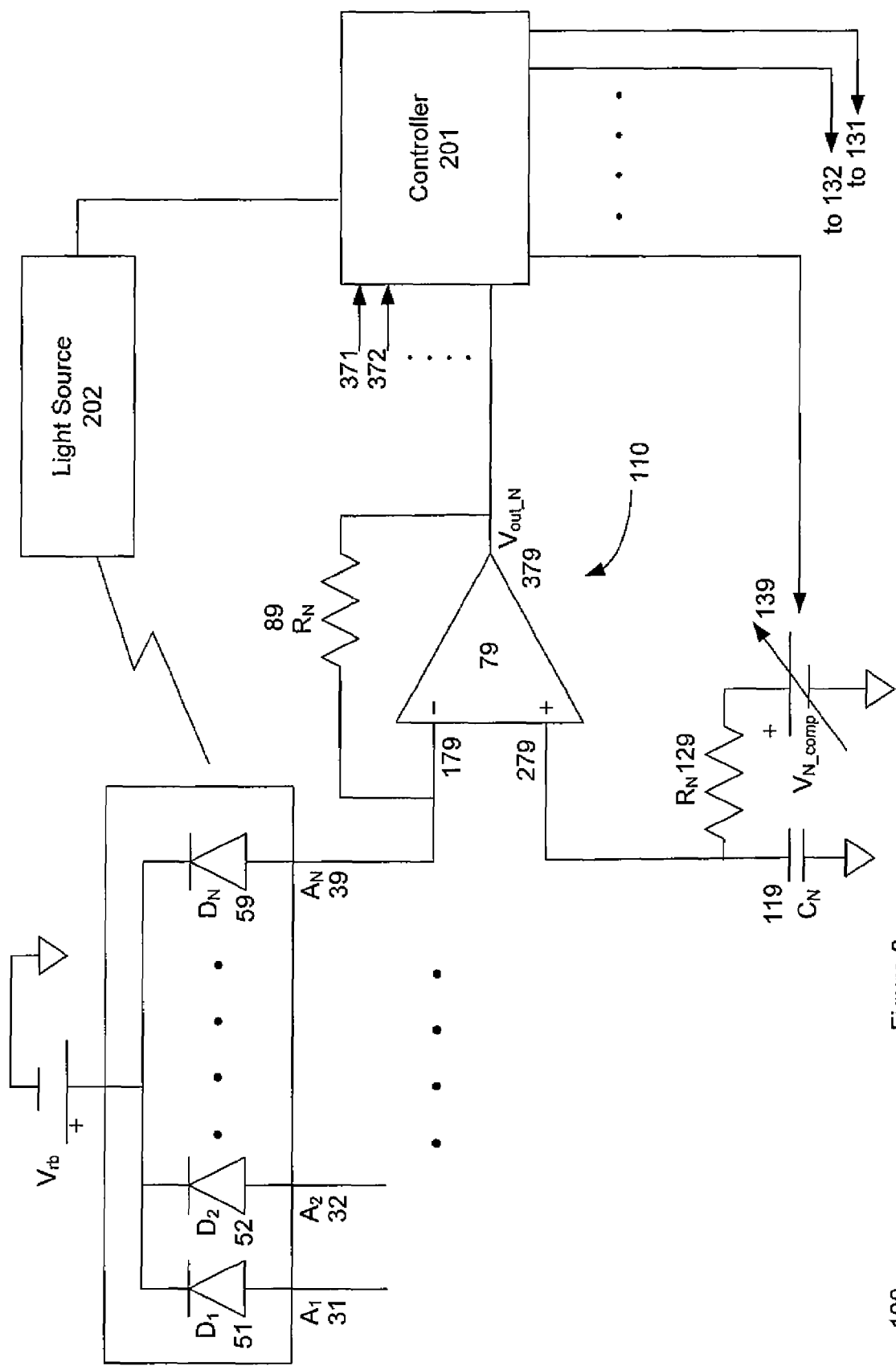
FIG. 3 illustrates a multiple sensor unit according to an embodiment of the invention.

FIG. 3 illustrates multiple sensor unit 100 according to an embodiment of the invention.

Multiple sensor unit 100 utilizes trans-impedance amplifiers for achieving low noise and also allows to controlling the characteristics of each single sensing diode, by virtually connecting each sensing diode to an adjustable voltage source, instead of being virtually grounded.

For simplicity of explanation only output circuit 199 that is connected to sensing diode DN 59 is shown, although each sensing diode (out of D1-DN 51-59) is connected to such an output circuit.

Output circuit 110 includes capacitor 119, resistor 129, adjustable voltage source 139 and operational amplifier 79' that includes a positive input 179, a negative input 279 and an output 379.

The cathode of sensing diode DN 59 is connected to a positive input 179 of operational amplifier 79. The DC voltage level at positive input 179 is virtually the same as the voltage at negative input 279 of operational amplifier 79. This voltage level is determined by an adjustable voltage source 139 that can be controlled by digital and/or analog means. For example this adjustable voltage source 139 can include a digital to analog converter.

Negative input 279 of operational amplifier 79 is connected to one end of capacitor CN 119 and to one end of resistor RN 129. The other end of resistor RN 129 is connected to the adjustable voltage source 139. The other end of capacitor 119 is grounded.

When a certain voltage VrefN is provided by adjustable voltage source 139 a negative voltage drop of Vrb-VrefN develops over sensing diode DN 59.

By altering the voltage supplied by adjustable voltage source 139 the inverse voltage over sensing diode DN 59 can be altered. Thus, if the sensing diode is an avalanche photo diode and its gain is lower than expected then the adjustable voltage source 139 can be adjusted to increase the inverse voltage over that sensing diode.

The output circuit 110 outputs an output signal VoutN (from output 379) that is responsive to the current that flows through DN 59 and to the voltage supplied by the adjustable voltage source 139.

FIG. 3 also illustrates a controller 201 and a light source 202. The controller receives output signals from multiple output circuits (illustrated by arrows marked 371, 372 and 379 and can also control a light source 202 to emit light that should be received by the sensing diodes D1-DN 51-59. It can provide the received output signals and determine how to adjust the adjustable voltage sources 131-139. Wherein adjustable voltage source 131 represents the adjustable voltage source that is virtually connected to D1 51 and adjustable voltage source 132 represents the adjustable voltage source that is virtually connected to D2 52.

The controller can evaluate the non-uniformity of sensing diodes D1-DN 51-59 based upon the relationship between the expected sensed light intensities and the output signals provided to controller 201, and in response, adjust the voltage provided by the adjustable voltage sources such as to compensate for non-uniformities.

Figure 4:
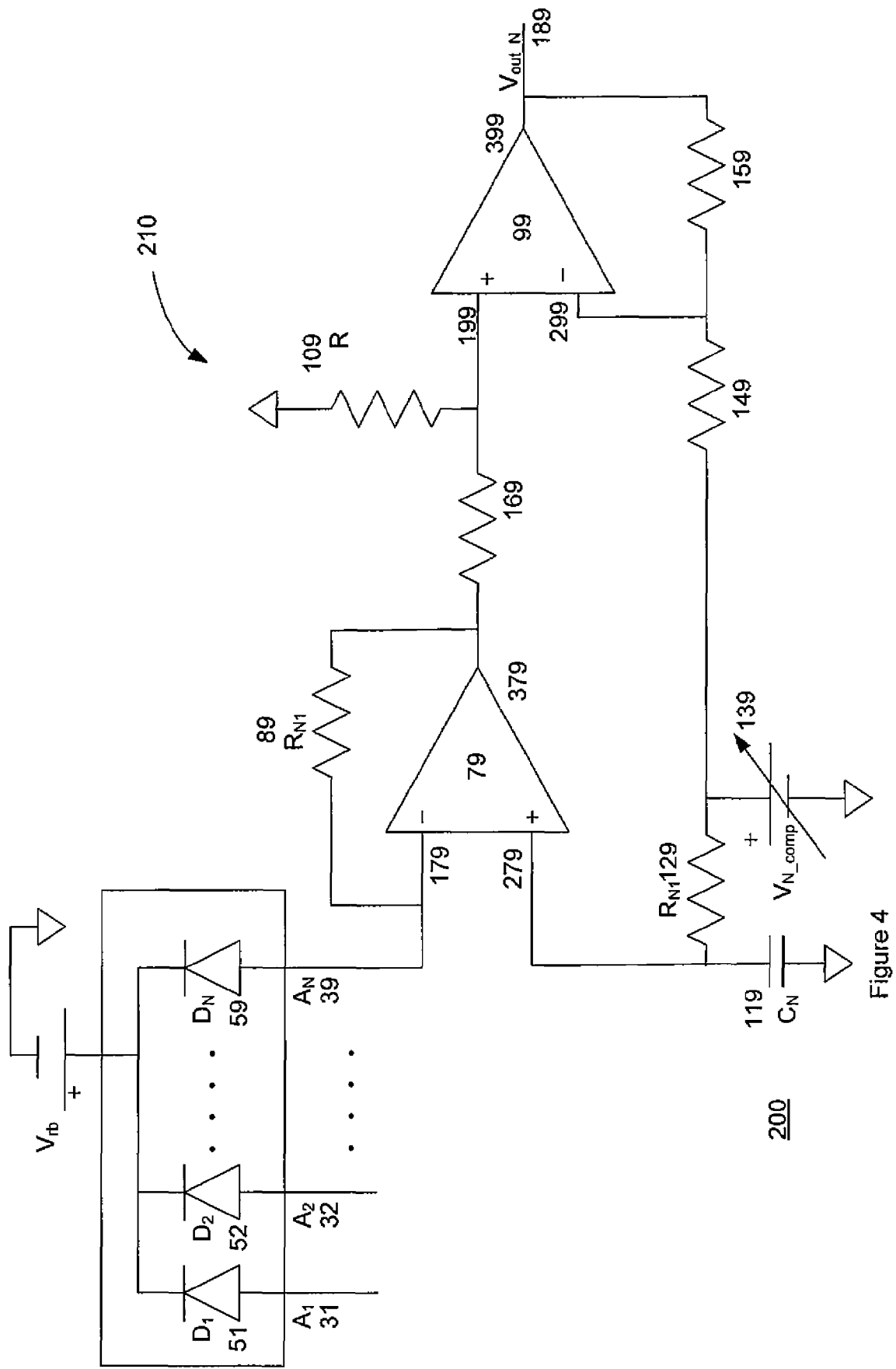
FIG. 4 illustrates a multiple sensor unit according to another embodiment of the invention.

FIG. 4 illustrates multiple sensor unit 200 according to another embodiment of the invention.

Multiple sensor unit 200 differs from multiple sensor unit 100 by providing an output signal VoutN 189 that is responsive to the current that flows through DN 59 and is not responsive to the voltage supplied by the adjustable voltage source 139. This is achieved by having (within output circuit 210) an additional operational amplifier stage that reduces the voltage supplied by the adjustable voltage source 139 from a sensing voltage that is responsive to the current flowing via sensing diode DN 59.

The additional operational amplifier stage includes resistors 149, 159, 169 and 109 and operational amplifier 99.

The output 379 of operational amplifier 79 is connected to a first end of resistor 169. The other end of resistor 169 is connected to a first end of resistor 109 and to a positive input 199 of operational amplifier 99. The other end of resistor 109 is grounded.

The other end of resistor RN1 129 is connected to the adjustable voltage source 139 and to one end of resistor 149. The other end of resistor 149 is connected to a negative input 299 of operational amplifier 99 and to a first end of resistor 159. The other end of resistor 159 is connected to an output 399 of operational amplifier 99 and forms an output of the circuit. It outputs a signal Vout 189 that is proportional to the current that flows through sensing diode DN 59.

According to other embodiments of the invention instead of connecting an output circuit to each sensing diode then some sensing diodes can share a single output circuit. This can reduce the ability to compensate sensing diode non-uniformity but can be more size efficient and less expensive.

FIG. 5 is a flow chart for method 200 according to an embodiment of the invention.

Method 200 starts by stage 210 of providing multiple sensing diodes adapted to convert light to current. Each sensing diode is coupled to an output circuit that includes a trans-impedance amplifier connected to an adjustable voltage source.

Stage 210 is followed by stage 220 of determining a voltage signal provided by each of the adjustable voltages sources such as to affect a sensing diode characteristic.

Conveniently, stage 220 includes determining the voltage signals provided by the adjustable voltages sources such as to compensate for non-uniformities between the sensing diodes.

Conveniently, stage 220 includes measuring the sensing diodes non-uniformities.

Stage 220 is followed by stage 230 of adjusting the adjustable voltage sources according to the determination.

Conveniently, stage 230 is followed by stages 240 or 250. These stages depend upon the configuration of the output circuits connected to the sensing diodes. If the output circuit resembles output circuit 199 then stage 230 is followed by stage 250. If the output circuit resembles output circuit 199' than stage 230 is followed by stage 250.

Stage 240 includes illuminating a wafer or a reticle and providing multiple output signals, whereas each output signal is responsive to a current that flows through a sensing diode and to a voltage signal provided by an adjustable voltage source coupled to that sensing diode.

Stage 250 includes illuminating a wafer or a reticle and providing multiple output signals, wherein each output signal is responsive to a current that flows through a sensing diode.

The present invention can be practiced by employing conventional tools, methodology and components. Accordingly, the details of such tools, component and methodology are not set forth herein in detail. In the previous descriptions, numerous specific details are set forth, such as shapes of cross sections of typical lines, amount of deflection units, etc., in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

I claim:

1. A system comprising:
    a plurality of sensing diodes adapted to convert light to a current output, wherein at least one of the sensing diodes is reversed-biased;
    a light source adapted to emit light to be received by the sensing diodes;
    a plurality of trans-impedance amplifier circuits, each trans-impedance amplifier circuit comprising an op-amp, and an impedance connecting an output of the op-amp to a first input of the op-amp;
    a plurality of adjustable voltage sources; and
    a controller adapted to control the light source to determine at least one diode characteristic and to adjust a corresponding adjustable voltage source so as to compensate for non-uniformities among the plurality of sensing diodes, wherein
    the current output of each sensing diode is coupled to a corresponding trans-impedance amplifier circuit by an electrical connection to a first input of a corresponding op-amp;
    a second input of the corresponding op-amp is coupled to a corresponding adjustable voltage source;
    the output of the corresponding op-amp is a signal responsive to a sensing voltage, and to a voltage signal provided by the corresponding adjustable voltage source, said sensing voltage being responsive to a current output of a corresponding sensing diode; and
    changes in a voltage signal provided by the corresponding adjustable voltage source affect a characteristic of the corresponding sensing diode.

2. The system according to claim 1 wherein the sensing diodes sense ultra-violet light.

3. The system according to claim 1 further comprising a second corresponding op-amp coupled to the corresponding trans-impedance amplifier circuit and to the corresponding adjustable voltage source, said second corresponding op-amp being adapted to output an output signal responsive to a sensing voltage responsive to a current developed by the corresponding sensing diode.

4. The system according to claim 1 further comprising a second corresponding op-amp coupled to the corresponding trans-impedance amplifier circuit and to the corresponding adjustable voltage source, adapted to subtract the voltage signal provided by the corresponding adjustable voltage source from an internal voltage signal, said internal voltage signal being responsive to the voltage signal provided by the corresponding adjustable voltage source and to the sensing voltage responsive to the current output of the corresponding sensing diode.

5. A method, comprising:
    converting light to a current output with a plurality of sensing diodes, wherein at least one of the sensing diodes is reversed-biased; and
    affecting a characteristic of a corresponding sensing diode with a corresponding trans-impedance amplifier circuit, said trans-impedance amplifier circuit comprising an op-amp, and an impedance connecting an output of the op-amp to a first input of the op-amp, the first input of the op-amp being electrically connected to a current output of the corresponding sensing diode and a second input of the op-amp being coupled to a corresponding adjustable voltage source, said affecting step comprising
    outputting a signal from the op-amp responsive to a sensing voltage, and to a voltage signal provided by the corresponding adjustable voltage source, said sensing voltage being responsive to the current output of the corresponding sensing diode, and
    changing the voltage signal provided by the corresponding adjustable voltage source using a controller adapted to control a light source adapted to emit light to be received by the sensing diodes to determine the characteristic of the corresponding sensing diode and to adjust the corresponding adjustable voltage source so as to compensate for non-uniformities among the plurality of sensing diodes.

6. The method according to claim 5 further comprising measuring non-uniformities among the plurality of sensing diodes.

* * * * *